United States Patent
Felton et al.

(10) Patent No.: US 12,076,243 B2
(45) Date of Patent: Sep. 3, 2024

(54) ADHESIVE PENILE CONSTRUCTION TEMPLATE AND URETHRA SCAFFOLD TUBE FOR NEOPHALLUS SURGERY

(71) Applicant: Boston Scientific Scimed, Inc., Maple Grove, MN (US)

(72) Inventors: Jessica Elizabeth Felton, Minneapolis, MN (US); Aaron Roydon Johnson, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1071 days.

(21) Appl. No.: 16/947,355

(22) Filed: Jul. 29, 2020

(65) Prior Publication Data
US 2021/0038389 A1    Feb. 11, 2021

Related U.S. Application Data

(60) Provisional application No. 62/883,205, filed on Aug. 6, 2019.

(51) Int. Cl.
*A61F 2/26* (2006.01)
*A61F 2/04* (2013.01)

(52) U.S. Cl.
CPC ............ *A61F 2/26* (2013.01); *A61F 2/04* (2013.01); *A61F 2002/047* (2013.01);
(Continued)

(58) Field of Classification Search
CPC . A61B 17/322; A61F 2/04; A61F 2/26; A61F 2002/047; A61F 2240/005
See application file for complete search history.

(56) References Cited

U.S. PATENT DOCUMENTS

| 6,626,865 B1 | 9/2003 | Prisell |
| 2007/0005128 A1 | 1/2007 | Scholz et al. |

(Continued)

FOREIGN PATENT DOCUMENTS

WO    2017192723 A1    11/2017

OTHER PUBLICATIONS

Invitation to Pay Additional Fees and Partial International Search Report for PCT Application No. PCT/US2020/070331, mailed Nov. 13, 2020, 12 pages.

(Continued)

*Primary Examiner* — Christine H Matthews
(74) *Attorney, Agent, or Firm* — Brake Hughes Bellermann LLP

(57) ABSTRACT

A penile construction template may include an adhesive film configured for adhesion to donor skin. The penile construction template may include a first section defined on the adhesive film to identify an external phallus skin flap of the donor skin to be extracted while the adhesive film is adhered to the donor skin, and a second section defined on the adhesive film to identify a de-epithelialized skin flap of the donor skin to be extracted while the adhesive film is adhered to the donor skin. An implantable device for urethra construction may include a tubular scaffold configured to be coupled to a natal urethra of a patient, the tubular scaffold being seeded with urethral cells of the patient for growth of a urethral segment on the tubular scaffold therefrom while disposed within a body of the patient.

8 Claims, 8 Drawing Sheets

(52) U.S. Cl.
CPC .............. *A61F 2210/0004* (2013.01); *A61F 2220/0016* (2013.01); *A61F 2230/0019* (2013.01)

(56) References Cited

U.S. PATENT DOCUMENTS

| | | | |
|---|---|---|---|
| 2016/0074186 A1* | 3/2016 | Sartor | ............... A61M 25/0017 623/23.65 |
| 2018/0098854 A1 | 4/2018 | Allen et al. | |
| 2018/0098855 A1* | 4/2018 | Crabb | ....................... A61F 2/26 |

OTHER PUBLICATIONS

Djordjevic, "Novel Surgical Techniques in Female to Male Gender Confirming Surgery", Translation Andrology and Urology, 7(4), 2018, pp. 628-638.

Hage, et al., "Fibula Free Flap Phalloplasty: Modifications and Recommendations", Wiley-Liss, Inc., Microsurgery 17, 1996, pp. 358-365.

Ladewig, et al., "Designing In Vivo Bioreactors for Soft Tissue Engineering", Journal of Biomaterials and Tissue Engineering, vol. 2, No. 1, Mar. 2012, pp. 1-13.

Orabi, et al., "Tissue Engineering of Urinary Bladder and Urethra: Advances from Bench to Patients", The Scientific World Journal, vol. 2013, Article ID 154564, Jan. 2013, 13 pages.

* cited by examiner

ADHESIVE PENILE CONSTRUCTION TEMPLATE AND URETHRA SCAFFOLD TUBE FOR NEOPHALLUS SURGERY

CROSS-REFERENCE TO RELATED APPLICATION

This application claims priority to U.S. Provisional Patent Application No. 62/883,205, filed on Aug. 6, 2019, entitled "ADHESIVE PENILE CONSTRUCTION TEMPLATE AND URETHRA SCAFFOLD TUBE FOR NEOPHALLUS SURGERY", the disclosure of which is incorporated by reference herein in its entirety.

TECHNICAL FIELD

This disclosure relates generally to penile construction.

BACKGROUND

In some examples, penile prostheses for erectile dysfunction have been used off-label in penile construction or reconstruction cases such as female to male transgender, and natal males with penile reconstruction (e.g., congenital disorders, amputation (penile cancer), trauma, etc.). For example, a patient undergoes a phalloplasty procedure (e.g., single stage or multiple stages) in which a neophallus is surgically constructed from tissue grafts taken from other parts of the body.

The creation of a penis generally involves the creation of a tube within a tube. The inside tube is the urethra, the structure through which men urinate. The outside tube is the penile shaft. This structure, known as the neophallus (neo- for new), is surgically attached to the pelvis. The urethra of the neophallus is connected to the existing urethra. The blood vessels and nerves are attached to those of the pelvis. The exterior of the neophallus is then sculpted to resemble a penis shaft and head.

The phalloplasty procedure may be considered highly invasive with relatively high infection risks, and a patient may be open on the operating table for an extended period of time (e.g., 8+ hours). Results depend highly on a skill level and approach of the surgeon performing the operation. Thus, a duration and complexity of the phalloplasty procedure may lead to unsatisfactory outcomes.

SUMMARY

According to an aspect, a method of implanting a neourethra attached to a natal urethra of a patient includes seeding a tubular scaffold with urethral cells of the patient. The method further includes disposing the seeded tubular scaffold within a body of the patient for subsequent in vivo growth of a neourethra and connecting the neourethra to the natal urethra.

According to an aspect, an implantable device for urethra construction includes a tubular scaffold configured to be coupled to a natal urethra of a patient. The tubular scaffold may be seeded with urethral cells of the patient for growth of a urethral segment on the tubular scaffold therefrom while disposed within a body of the patient.

According to an aspect, a penile construction template may include an adhesive film configured for adhesion to donor skin. The penile construction template may include a first section defined on the adhesive film to identify an external phallus skin flap of the donor skin to be extracted while the adhesive film is adhered to the donor skin, and a second section defined on the adhesive film to identify a de-epithelialized skin flap of the donor skin to be extracted while the adhesive film is adhered to the donor skin.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants, and methods of making and/or surgically implanting such bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
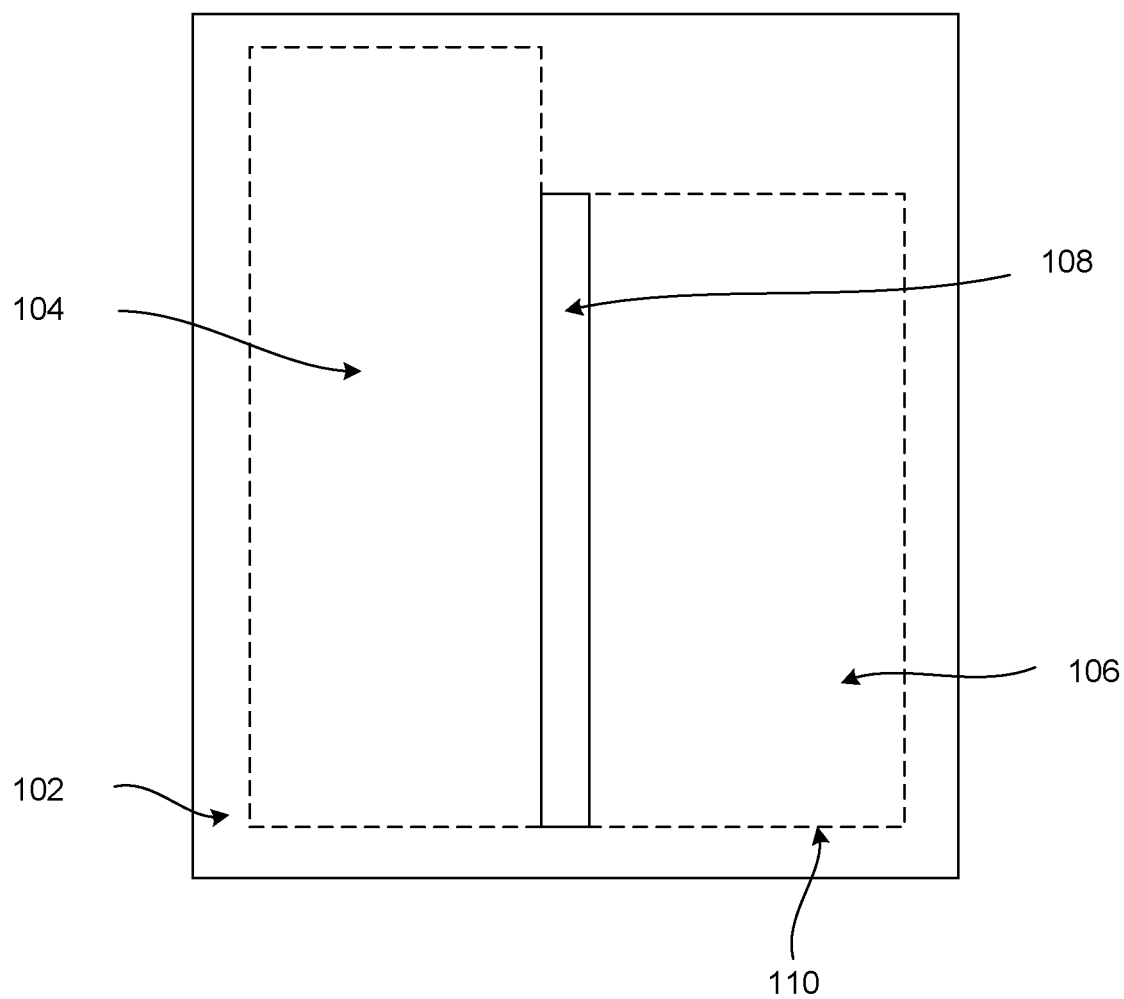
FIG. 1 illustrates an adhesive penile construction template for phalloplasty procedures, according to an aspect.

FIG. 1 illustrates an adhesive penile construction template 100 for phalloplasty procedures, according to an aspect. According to example aspects, the adhesive penile construction template 100 includes, and may be at least partially constructed using, a film 102 that may be an anti-microbial and sterilizable film.

When attached to a donor area of skin of a patient, the adhesive penile construction template 100 defines an area of donor skin that can be extracted (together with associated tissues) and used to form a neophallus for the patient during a phalloplasty procedure. The adhesive penile construction template 100 defines all necessary skin areas required by a surgeon to proceed with the phalloplasty procedure. Moreover, as referenced herein, the resulting, defined skin areas are individually and proportionally sized for use during the phalloplasty procedure.

Figure 3:
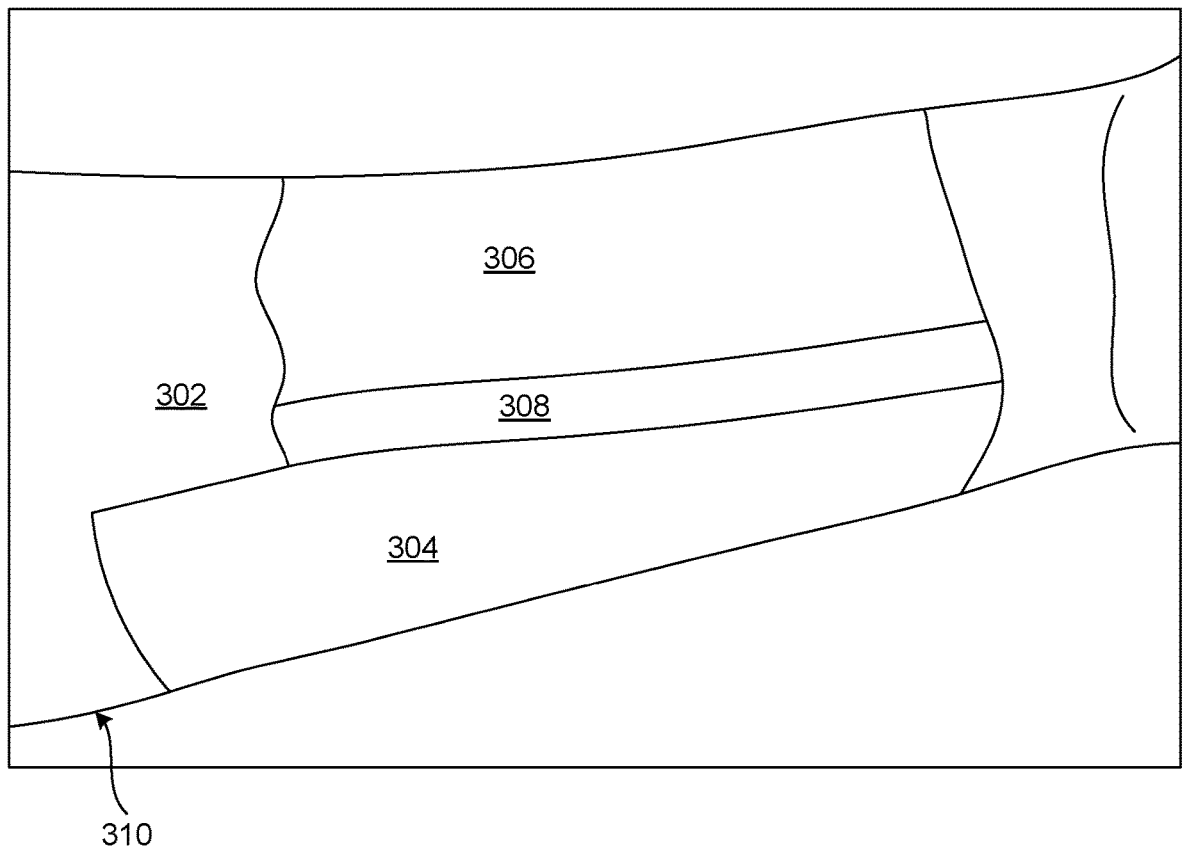
FIG. 3 illustrates an implementation of the adhesive penile construction template of FIGS. 1 and 2, used in conjunction with a forearm of a patient.

As further illustrated in FIG. 1, the adhesive penile construction template 100 may include a urethra section 104. That is, the phrase "urethra section" should be understood to refer to a urethra-forming section of the adhesive penile construction template 100 used to As referenced above, and described and illustrated below in more detail, the urethra section 104 may be adhered to a donor skin area of a patient (as illustrated in the example of FIG. 3), and thereby used to define an area of patient skin to be cut, extracted, and rolled for use during the phalloplasty procedure to form a new, extended urethra for the patient. Thus, for clarity of description, the defined area of patient skin and associated tissues removed using the urethra section 104 may be referred to herein as a "urethra flap." Put another way, using the template shape formed by the urethra section 104 while adhered to the donor skin area of the patient, a surgeon or other medical personnel may easily, reliably, and quickly determine an underlying area to be removed to obtain the urethra flap, rolled, and attached to a natal urethra of a patient, to thereby form a new, extended urethra for the patient.

As may be observed in FIG. 1, the urethra section 104 is generally rectangular in shape, with a length that extends in parallel to a length of an external phallus section 106, and to a length of a de-epithelialized section 108, both of which are described in detail, below. In the example of FIG. 1, the length of the urethra section 104 is greater than the width of the urethra section 104. Further, the length of the urethra section 104 is longer than the substantially-equal lengths of the de-epithelialized section 108 and the external phallus section 106, where the relatively greater length of the urethra section 104 may be understood to be useful in facilitating attachment of the corresponding urethra flap (once rolled to form a new urethra portion) to the natal urethra of the patient.

The external phallus section 106 is an adhesive portion of the adhesive penile construction template 100 that, when adhered to the donor area of the skin of the patient, defines a skin portion to be removed with associated tissues, rolled, and used as an external phallus. For purposes of clarity of description, the thus-defined skin and tissues are referred to herein as "external phallus flap." Put another way, skin and tissues removed using the external phallus section 106 (i.e., the external phallus flap) may be rolled in conjunction with the urethra flap obtained using the urethra section 104, during a phalloplasty procedure, to thereby form an outer or exterior portion of the neophallus. Put another way, and as illustrated below, with respect to FIGS. 4A-4D, the external phallus flap obtained using the external phallus section 106 is used to define an area of patient skin/tissues that will form the outer tube of the neophallus, while the urethra flap obtained using the urethra section 104 is used to form the inner tube of the neophallus.

The de-epithelialized section 108 is illustrated as being positioned between the urethra section 104 and the external phallus section 106. The de-epithelialized section 108 is an adhesive portion of the adhesive penile construction template 100 that, when adhered to the donor area of the skin of the patient, defines a portion of skin and tissues to be removed and de-epithelialized, prior to rolling of the urethra flap and the external phallus flap to form the neophallus. For purposes of clarity of description, the thus-defined skin and associated tissues are referred to herein as "de-epithelialized flap."

As described below, the de-epithelialized section 108 has a length that is substantially equal to the length of the external phallus section 106. A width of the de-epithelialized section 108 is substantially less than the widths of both of the urethra section 104 and the external phallus section 106. More specifically, in some example implementations, the width of the de-epithelialized section 108 is defined to be minimally sufficient to enable satisfactory attachment (e.g., suturing) of outer edges of the rolled urethra flap and the rolled external phallus flap thereto during formation of the neophallus.

The adhesive penile construction template 100 may be pre-defined and pre-constructed, prior to commencement of a phalloplasty procedure. The adhesive penile construction template 100 relieves the performing surgeon of a requirement to manually define sizes and/or proportions of the urethra flap, external phallus flap, and de-epithelialized flap to be obtained for use in forming the neophallus. Moreover, the adhesive penile construction template 100 is highly customizable, so that many different sizes and proportions may be available for selection, while ensuring that such available sizes/proportions are within ranges that will provide results that are medically acceptable.

In general, a phalloplasty can be performed in a single stage or in multiple stages. A single stage phalloplasty involves the simultaneous construction of the phallus and urethra, as well as the connection of the urethra. Where relevant, it also involves the creation of a scrotum and insertion of testicular prostheses. All of this is done as a single procedure, although any penile prostheses are generally put in at a later date.

A multi-stage phalloplasty breaks the surgery down into parts. This is more common, as it allows for more detailed management of each part of the surgery. However, some surgical teams do perform single-stage procedures. This can be more convenient for patients who have to travel a significant distance for surgery.

As referenced above, with the specialization of the phalloplasty procedure, there is a lack of standardization in tissue skin graft size and shape for an appropriate neophallus. In conventional approaches, during the phalloplasty, an entire donor flap is free-hand measured with a ruler and sketched with surgical markers on the patient's skin. The size and shape thus depend entirely on how the surgeon draws and cuts the tissue graft, as well as the thickness of the tissue. As a result, an end size may not be fully determined until the graft is removed and rolled into the tube. In some cases, in conventional approaches, the neophallus may be wider than it is long which has an unnatural look and is undesirable. Also, in conventional approaches, the donor skin is sterilized, e.g., using iodine wipes, and the markings may be removed or smeared with such application or iodine or other antiseptic measures. In such scenarios, the image must be redrawn, but more carefully so as to minimize potential contamination.

In contrast, when using the adhesive penile construction template 100 of FIG. 1, surgical time may be decreased. For example, as referenced above, the adhesive penile construction template 100 is pre-defined, so that the surgeon does not need to measure donor skin with a ruler, and/or draw on the patient's skin (e.g., arm).

The adhesive penile construction template 100 is smear-proof and anti-microbial, so that the surgeon does not need to wipe down a drawn area with iodine, thereby smearing any drawing and requiring re-measuring and re-drawing the required dimensions. Moreover, infection risks may be reduced, due to the imbedded anti-microbial within the film 102 over the cut areas of the skin.

Standardization of skin grafts using the adhesive penile construction template 100 provides more consistent results across multiple phalloplasty procedures. For example, a surgeon may be provided with an ability to choose one of multiple sizes offered, and to make a selection based on the graft location on the patient's body and/or the desired neophallus length. A size of the adhesive penile construction template 100 may vary on various factors, such as the limb from which the skin graft is being harvested, as well as the size of the desired neophallus.

The adhesive penile construction template 100 is also less frustrating to a surgeon and nursing staff. For example, the adhesive penile construction template 100 provides a one-and-done picture to be used, as compared to standard techniques using surgical markers. In particular, surgical markers may run out of ink, or have a short lifespan, or may intermittently be difficult to use to write on human skin.

In the example of FIG. 1, the adhesive penile construction template 100 is illustrated as including dashed lines defining a perimeter of a total neophallus flap area 110 that includes the areas of the urethra section 104, the external phallus section 106, and the de-epithelialized section 108. In other words, by cutting along the dashed lines illustrated as defining the neophallus flap area 110 (using a scalpel or other suitable cutting tool), the surgeon may remove an entire skin flap that includes the urethra flap, the external phallus flap, and the de-epithelialized flap.

In some example implementations, the adhesive penile construction template 100 may be removed from the skin flaps following cutting of the skin flap(s). In other examples, the adhesive penile construction template 100 may be bioresorbable, and may be retained on the skin surfaces following the cutting of the skin flap(s) and through the rolling and other construction of the neophallus.

In such implementations, portions of the retained template film may effectively form a lumen of the new urethra, and may minimize unwanted hair growth within the new urethra. Further, the anti-microbial properties and other aspects of the template film 102 may be useful in facilitating healing following the phalloplasty procedure.

According to some aspects, all of the three sections 104, 106, 108, or an entirety of the template film 102, may be substantially identical with respect to material or physical properties thereof. For example, the template film 102 may have the same degree of adhesion across an entire surface thereof that attaches to the patient's skin.

In other examples, the sections 104, 106, 108 may have physical or material properties or aspects that differ from one another, and/or from an area of the template film 102 that is outside of the perimeter 110. For example, the sections 104, 106, 108 may have a lower degree of adhesion than the area of the template film 102 outside of the perimeter 110, to ensure secure adhesion of the film 102 as a whole to the patient's skin, while still facilitating removal of the sections 104, 106, 108 from the skin flap(s) once cut and prior to rolling thereof to form the neophallus.

Conversely, in other implementations, the sections 104, 106, 108 may have a higher degree of adhesion than a remainder of the film 102 outside of the perimeter 110. For example, as referenced above, it may be desirable to leave the portions of the template film 102 defining the sections 104, 106, 108 adhered to the obtained skin flap(s) following removal of the obtained skin flap(s), e.g., in scenarios where the film 102 is bioresorbable.

Further, physical or material properties or aspects of the various sections 104, 106, 108 may differ from one another. For example, the different sections 104, 106, 108 may be configured to peel off separately from one another, and may individually contain features to perform specific, relevant functions. For example, different ones of the sections 104, 106, 108 may include features to reduce hair growth, promote healing, or prevent infection, where such features may be customized in extent and kind with respect to each of the sections 104, 106, 108.

In particular implementations, for example, materials in the urethral section 104 may contain substances known to reduce hair growth, such as depilatory creams and/or hair growth inhibitors. In other examples, one or more of the sections may include elude drugs, or other suitable healing agents.

Although the adhesive penile construction template 100 is described above in the context of phalloplasty procedures, it will be appreciated that such examples are non-limiting, and that the adhesive penile construction template 100 may be utilized in other contexts. For example, corresponding adhesive templates may be used to implement temporary tattoos. For example, the template and ink may also be used as a temporary tattoo in which the film/sticker is removed, while the smear-proof ink template remains on the skin, with a selected design printed thereon.

Figure 2:
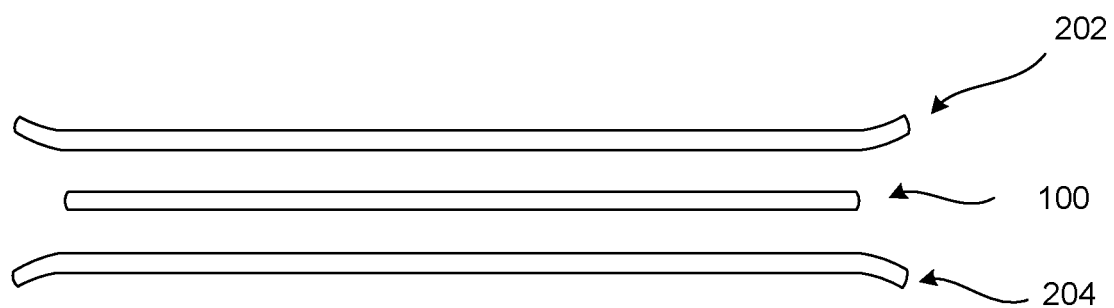
FIG. 2 illustrates a cross section of the adhesive penile construction template of FIG. 1.

FIG. 2 illustrates a cross-section of the adhesive penile construction template 100 of FIG. 1. In the example of FIG. 2, the adhesive penile construction template 100 is made up of two protective sheets 202, 204, attached in the example to a top and bottom surface, respectively, of the adhesive penile construction template 100.

The protective sheets 202, 204 may be utilized to protect the adhesive penile construction template 100 from external forces that may occur, up to a point of use. As shown, the adhesive penile construction template 100 may be positioned between the two protective layers, e.g., to minimize damage, to prevent the image from smearing, and to aid in placement onto the skin.

To use the adhesive penile construction template 100 in the example of FIG. 2, the surgeon may first remove the bottom protective layer 204, to expose the adhesive side of the template. The adhesive penile construction template 100 may then be placed, adhesive side down, onto the skin at the desired location, as shown in FIG. 3.

Then, the top protective layer 202 may be removed to reveal the translucent film on skin, with the adhesive penile construction template 100 template marked in sterile, smear-proof ink. The sturdiness of the top protective layer 202 may be configured to aid in a placement of the adhesive penile construction template 100 on the skin of the patient. The adhesive penile construction template 100 may remain adhesively bonded to the skin while the surgeon dissects the skin flap. As described above, the adhesive penile construction template 100 may be removed by peeling it off following dissection of the skin flap(s), or may stay adhered throughout (and following) the phalloplasty procedure(s).

FIG. 3 illustrates an implementation of the adhesive penile construction template 100 of FIGS. 1 and 2, used in conjunction with a forearm of a patient. In the example of FIG. 3, adhesive template film 302 is illustrated as a transparent film adhered to a forearm 310 of a patient.

As referenced above, in some implementations, the adhesive template film 302 may be constructed using adhesive surgical drape material, with embedded iodine for antimicrobial purposes. As may be observed in FIG. 3, urethra section 304, external phallus section 306, and de-epithelialized section 308 are visibly drawn on the adhesive template film 302.

Although the example of FIG. 3 illustrates the forearm 310, other areas of the body may be used for donor skin flaps. For example, the forearm 310, e.g., the radial forearm, provides one example of using a 'free flap', in which the obtained tissue is disconnected from the blood supply for transfer to the genital region, and then reconnected to local arteries and veins using microsurgery. In other examples, another form of skin flap that may be used is known as the pedicle flap, where the obtained tissue remains connected to the blood supply. This type of flap does not require microsurgery anastomosis, since the vessels remain connected.

Figure 4A:
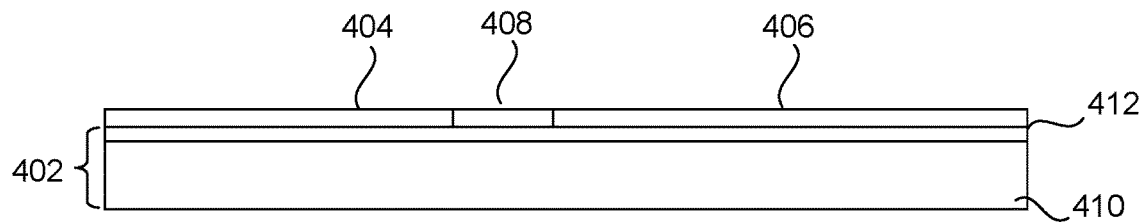
FIG. 4A illustrates a cross section of an example implementation of an adhesive penile construction template of FIGS. 1-3, attached to a patient skin flap.

FIG. 4A illustrates a cross section of an example implementation of an adhesive penile construction template of FIGS. 1-3, attached to a patient skin flap 402, including an epidermis 412 and dermis/subcutaneous tissue 410. In the example of FIG. 4A, a urethra section 404, a de-epithelialized section 408, and an external phallus section 406 are illustrated.

FIG. 4A further illustrates a cross section of a patient skin flap 402 obtained through the use of the adhesive penile construction template of FIG. 4A, according to an aspect, and that may be used in associated phalloplasty procedures. For example, the patient skin flap 402 may be obtained by cutting along a perimeter of the sections 304, 306, 308 of FIG. 3 to obtain the patient skin flap 402 from the forearm 310.

Figure 4B:
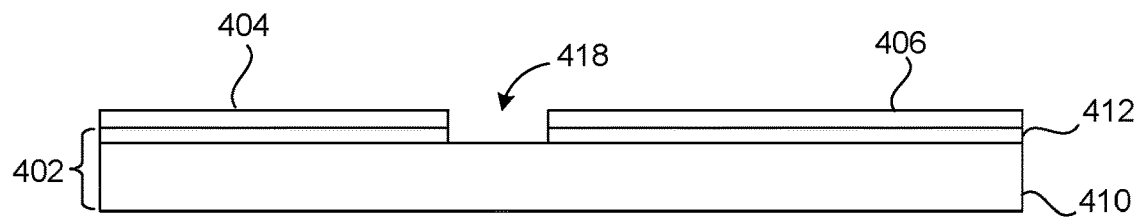
FIG. 4B illustrates a cross section of a patient skin flap obtained through the use of the adhesive penile construction template of FIG. 4A, according to an aspect, and that may be used in associated phalloplasty procedures.
Figure 4C:
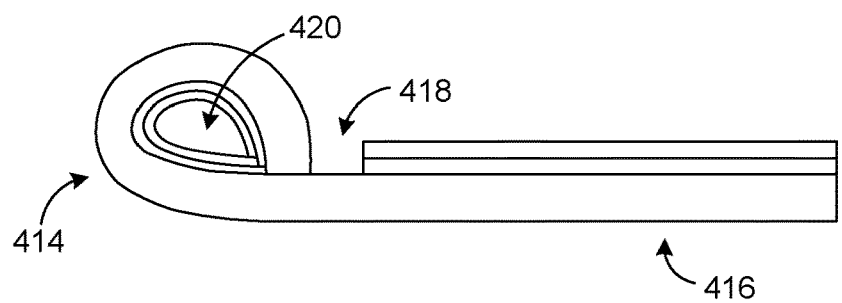
FIG. 4C illustrates the cross section of patient skin flap of FIG. 4B, rolled to form a urethra.

In FIG. 4B, an opening is defined using the de-epithelialized section 408, which exposes a de-epithelialized flap 418. In FIG. 4C, a urethra flap 414 of the patient skin flap 402 is illustrated as being aligned with the urethra section 404 of FIGS. 4A and 4B. An external phallus flap 416 of the patient skin flap 402 is illustrated as being aligned with the external phallus section 406 of FIGS. 4A and 4B.

In the patient skin flap 402, an epidermis 412 is illustrated. As illustrated in FIG. 4B, the epidermis 412 is not present within the de-epithelialized flap 418, having been removed during a de-epithelization process. A dermis (and associated subcutaneous tissue) 410 is also illustrated as forming part of each of the flaps 414, 416, 418.

FIG. 4C illustrates the cross section of patient skin flap 402 of FIG. 4B, rolled to form a urethra (inner tube) 420. For example, the urethral graft section may be rolled around a Foley® catheter. In other implementations, some of which are described and illustrated below with respect to FIGS. 5-7, a scaffold may be used.

In the example of FIG. 4C, the edge of the urethra flap 414 is sutured to the edge of the de-epithelialized flap 418, so that the urethra flap 414 is mated with the dermis and subcutaneous tissue 410. The resulting tube forms the neourethra 420.

Figure 4D:
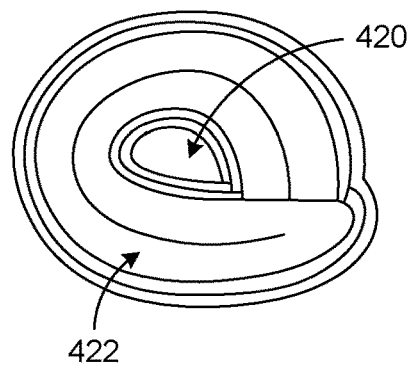
FIG. 4D illustrates the cross section of patient skin flap of FIG. 4C, further rolled to form an entire neophallus.

The external phallus flap 416 is wrapped around the urethral flap 414 and sutured to the other edge (i.e., remaining exposed portion) of the de-epithelialized flap 418, as shown in FIG. 4D. Thus, in the resulting external phallus 422, only epidermis is on the exterior of the neophallus.

Figure 5:
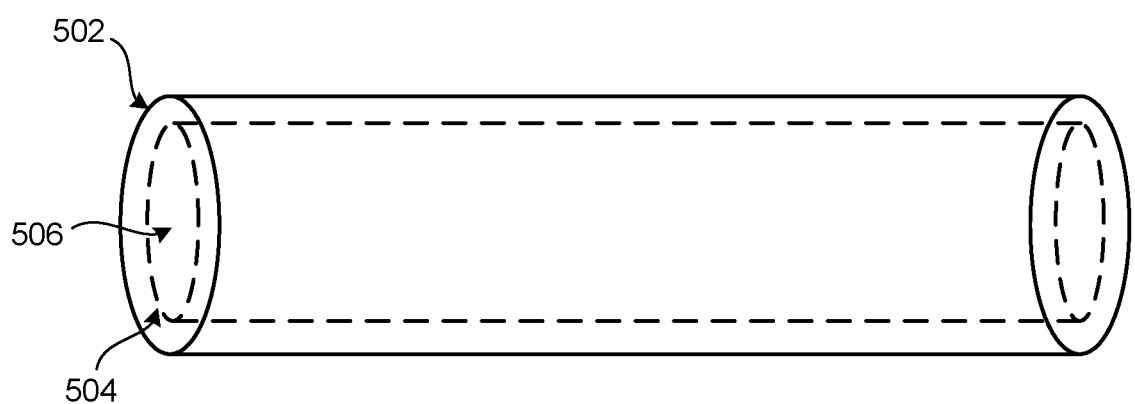
FIG. 5 illustrates a tubular scaffold that may be used to generate at least a portion of a urethra of a patient, which may be used in conjunction with the phalloplasty procedures of FIGS. 1-4.

FIG. 5 illustrates a tubular scaffold 500 that may be used to generate at least a portion of a urethra of a patient, which may be used in conjunction with the phalloplasty procedures of FIGS. 1-4. As illustrated, the scaffold 500 includes an outer surface 502 and an inner surface 504, which together define an inner tube 506 for formation of a urethral lumen.

As described in detail, below, the scaffold 500 is composed of a bioreactive material that may be seeded with urethral cells and implanted into a patient's body to extend, or replace at least a portion of, the patient's urethra. The patient's body may serve as an in vivo bioreactor to enable and facilitate urethral growth, while the scaffold 500 may be composed of a bioabsorbable or biodegradable material that degrades while the new urethral growth occurs. The tubular scaffold 500 may be trimmed to any length to fit the anatomy of the patient, or to perform other duties than just neophallus creation, such as urethral stricture or fistula repair.

Use of the scaffold 500, and associated techniques and procedures (as referenced above and described in detail, below), provides a number of advantages. For example, as referenced above, phalloplasty procedures are generally considered to be highly invasive, with high infection rates, and require a patient to be open on the operating table for eight or more hours at a time. Even following an ostensibly successful phalloplasty procedure, a patient may be required to undergo one or more revision surgeries, even for procedures that were intended to be single-stage.

For example, many such neophallus complications and revision surgeries are due to infections or other issues with the neourethra. Such issues may occur days, months, or years following the phalloplasty procedures.

For example, urethral stricture, which is a narrowing of the urethra, and which restricts the flow of urine from the bladder, may cause inflammation or infection. In some cases, urethral stricture may develop into a complete blockage and lead to urinary retention.

Another issue that presents itself long term is due to undesired hair growth within the neourethra. For example, although steps may be taken to remove all hair from an epidermis of a skin flap being used (such as the skin flap 402 of FIG. 4B), hair follicles within the dermis may remain or regrow within the neourethra lumen after healing, leading to an increased risk of infections and pain. Further, hair inside the neourethra may form 'hairballs' that require surgical removal.

The tubular scaffold 500, seeded with a patient's urethral cells and directly implanted into the patient's body, may thus replace a urethra segment, or lengthen the urethra in the application of neourethra. The patient's body acts as the bioreactor, and provides new blood vessels through in situ vascularization and associated tissue growth.

For example, according to an aspect, the tubular scaffold 500 may be disposed within a patient's body while the neourethra segment forms. In some example implementations, the seeded tubular scaffold may initially be disposed within one part of the patient's body, such as a forearm, calf, or peritoneal cavity, and then later removed/transplanted for connecting to the natal urethra of the patient. In other example implementations, the seeded tubular scaffold 500 may be connected to the natal urethra of the patient, and the neourethra may develop in situ, without a need for transplantation. In other implementations, the scaffold could be placed at a donor site and allowed to heal before the surgery, which may be referred to as a pre-laminated urethra. Then, at the time of the neophallus surgery, the prelaminated urethra may be taken as part of the skin flap.

Figure 6:
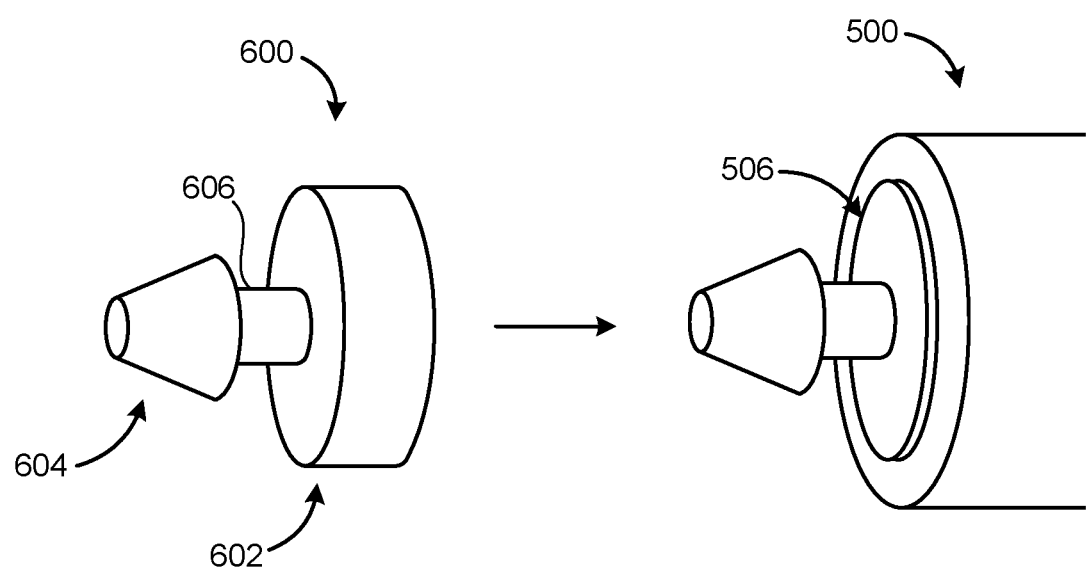
FIG. 6 illustrates a hose barb that may be used in conjunction with the tubular scaffold of FIG. 5.

FIG. 6 illustrates a hose barb 600 that may be used in conjunction with the tubular scaffold 500 of FIG. 5. The hose barb 600 generally enables a push-connection in which insertion is easier than removal, so that one end of the hose barb 600 may be inserted into the tubular scaffold 500 while an opposing end of the hose barb 600 may be inserted into the natal urethra of the patient.

In the example of FIG. 6, the hose barb 600 may include a cylindrical base 602 that is configured to be disposed within the neourethral lumen 506. The hose barb 600 may also include cone 604, attached to the cylindrical base 602 by a connecting cylinder 606. In the example of FIG. 6, the connecting cylinder 606 has a diameter that is smaller than a diameter of the cone 604, which is itself smaller than a diameter of the cylindrical base 602.

Following insertion of the cylindrical base 602 into the neourethral lumen 506, as shown in FIG. 6, the cone 604 may be inserted into, and push-connected with (and sutured together with), a natal urethra of the patient (shown in FIG. 6). In this way, pull-out of the hose barb 600 from either the scaffold 500 or the natal urethra is prevented.

Similarly to the scaffold 500, the hose barbs 600 may be biodegradable, with a degradation rate that approximately matches a rate of cell growth within the scaffold 500. In this way, the connection between the natal urethra and the neourethra may be maintained throughout a growth process of the neourethra.

In example implementations, the hose barb 600 may be placed into the end(s) of the scaffold 500 following a trimming of the scaffold 500 to its desired length. For example, the scaffold 500 may be trimmed to a length necessary to replace small segments of urethra during urethra repair, as may occur, for example, in response to urethra strictures. In other examples, during creation of a neophallus as described above, the scaffold 500 may be implanted into an area of a skin flap as a staged procedure. For example, the flap and neourethra may be harvested together and rolled into a neophallus, as describe with respect to FIGS. 1-4D. Once transferred to the genital area, the neourethra formed by the scaffold 500, including the patient's own tissue, may be attached to the patient's native urethra, e.g., using the hose barb 600.

Although FIG. 6 illustrates the example of the hose barb 600, other connections may be used, as well. For example, a stent-like end that can expand and hold open the urethra opening/connection point and anchor in the neourethra may be used. In other examples, other types of barbs or hooks may be used to attach to the native urethra, or may be suture-able for anastomosis with the patient's native urethra. Other connecters/couplers may be used to perform end-to-end anastomosis (such as anastomosis couplers sometimes used in surgery) of the native urethra with the tubular scaffold 500.

Figure 7:
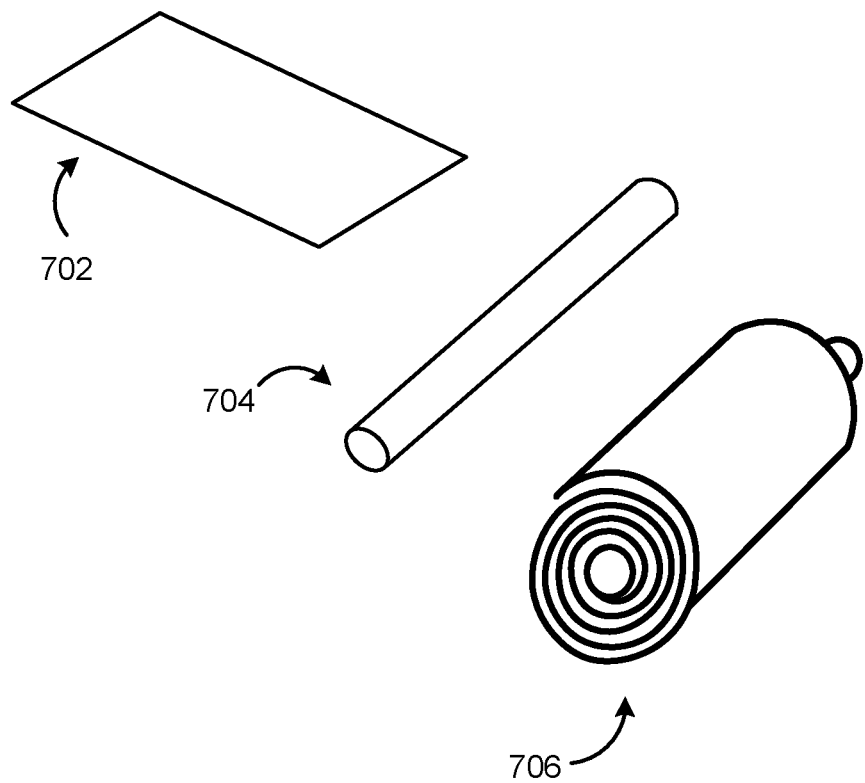
FIG. 7 illustrates a portion of an example method for constructing the tubular scaffold of FIG. 5.

FIG. 7 illustrates a portion of an example method for constructing the tubular scaffold 500 of FIG. 5. In FIG. 7, a matrix sheet 702 may be rolled around a mandrill 704 to obtain a rolled tubular scaffold 706, which may be seeded with a patient's urethral cells, as described above.

In general, scaffolds such as those referenced and described with respect to FIGS. 5-7 facilitate the delivery of cells to sites in the body, while providing a three-dimensional structure for the formation of new tissues with that structure, and while also providing support for the newly generated tissues. Scaffolds may be synthetic (e.g., using synthetic polymers), or may be biologically derived.

Although it is possible to culture a seeded scaffold in a bioreactor in vitro and perform subsequent in vivo implantation, the techniques described herein utilize the patient's body as the bioreactor. Consequently, in situ vascularization and associated tissue development may be induced, and a need for in vivo implantation may be removed.

Thus, the techniques of FIGS. 6-7 use the patient's natural tissue to create a neourethra, and reduce urethral complications from neophallus surgery, such as hair growth, infections, or urethral strictures. The described techniques also reduce scar tissue typically associated with urethral repair of urethra strictures (or other types of urethra repair, such as urethra fistula repair).

In the context of general urethral repair, the described techniques provide neourethra segments that are trimmable to desired lengths. Such segments may thus be used for multiple urethra repair and urethral lengthening procedures for a single patient. In all such procedures, the segment(s) mate with, and grow into, the patient's natural urethra. Further, surgical time and complications are reduced, because a surgeon is not required to transplant and/or roll skin, or collect other tissues, to create a neourethra, or neourethra segment.

In the context of phalloplasty procedures described above with respect to FIGS. 1-4D, the described techniques provide a natural appearance of a resulting neophallus, while allowing flexible, customizable adjustments to accommodate a desired length or other anatomical aspect(s).

The techniques of FIGS. 5-7 may be used in conjunction with the neophallus procedures of FIGS. 1-4D in various manners. For example, the adhesive penile construction template(s) of FIGS. 1-4 may be used and/or modified to incorporate the neourethral techniques of FIGS. 5-7.

For example, the adhesive penile construction template 100 of FIG. 1 may be modified to remove the urethra section 104. In these examples, the de-epithelialized section 108 and the external phallus section 106 may be used to collect appropriately-sized de-epithelialized flap 418 and external phallus flap 416 of FIGS. 4B-4D, without required collection of the urethral flap 414. Then, the collected external phallus flap 416 may be rolled around the seeded scaffold 500 of FIG. 5, and the resulting neophallus may be inserted into the natal urethra of the patient using, e.g., the hose barb 600 of FIG. 6.

In these and related examples, less skin (i.e., smaller skin flaps) are required to be removed from the patient. Further, the problems associated with unwanted hair growth within the urethral lumen are reduced, as compared to the techniques of FIGS. 1-4D. Still further, an overall neophallus procedure time may be reduced, because, as just referenced, the surgeon is no longer required to roll skin or collect other tissues to create the neourethra.

In other example embodiments, the adhesive penile construction template 100 may still be used as pictured in FIGS. 1 and 3, and using the rolling techniques of FIG. 4. In these embodiments, the urethral flap may be rolled around the seeded tubular scaffold 500, so that the seeded tubular scaffold is within the urethral lumen 420 of FIG. 4. In these embodiments, the urethra section 404 may remain on the urethra flap 414 and may be adhesive or otherwise configured to facilitate attachment to the tubular scaffold 500.

Figure 8:
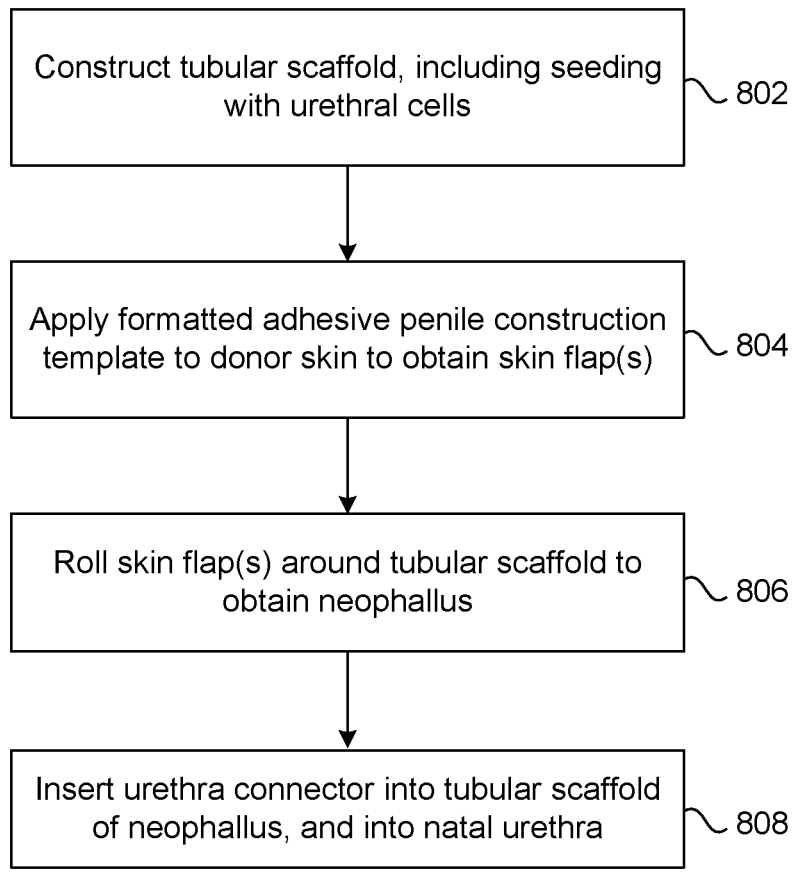
FIG. 8 is a flowchart illustrating example methods of performing phalloplasty procedures, using the examples of FIGS. 1-7.

FIG. 8 is a flowchart illustrating example methods of performing phalloplasty procedures, using the examples of FIGS. 1-7. Although FIG. 8 is illustrated as a sequence of discrete operations, it will be appreciated that various implementations of the illustrated methods of FIG. 8 may include additional or alternative operations. Further, any of the illustrated operations may be performed as two or more sub-operations, and, in some implementations, one or more operations or sub-operations may be omitted.

In the example of FIG. 8, a tubular scaffold is constructed, including seeding the tubular scaffold with urethral cells (802). For example, as described above, the tubular scaffold 500 may be constructed, using the techniques of FIG. 7, or other suitable techniques. Seeding of the tubular scaffold may proceed with donor urethral cells from the patient.

A formatted adhesive penile construction template may be applied to donor skin of the patient to obtain skin flap(s) (804). For example, the adhesive penile construction template 100 of FIG. 1 may be utilized. In other implementations, as referenced above, the urethra section 104 of the adhesive penile construction template 100 may be omitted.

Skin flap(s) obtained from cutting the donor skin based on the adhesive penile construction template may then be rolled around the tubular scaffold, to obtain a neophallus (806). In implementations in which a patient's urethra is being repaired, extended, or replaced without construction of a neophallus, operations 804 and 806 may be omitted.

A urethra connector may be inserted into a neourethra of the neophallus and into the natal urethra (808). For example, the cylindrical base 602 of the hose barb 600 of FIG. 6 may be inserted into the neourethra (tubular scaffold), while the cone 604 of the hose barb 600 may be inserted into the natal urethra.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A method of implanting a neourethra attached to a natal urethra of a patient, comprising:
   seeding a tubular scaffold with urethral cells of the patient;
   disposing the seeded tubular scaffold within a body of the patient for in vivo growth of a neourethra;
   removing the neourethra following the in vivo growth; and
   connecting the neourethra to the natal urethra following the removal of the neourethra.

2. The method of claim 1, wherein the connecting includes connecting the neourethra to the natal urethra using a hose barb.

3. The method of claim 1, wherein the tubular scaffold is biodegradable.

4. The method of claim 1, wherein the connecting comprises:
   rolling a skin flap obtained from donor skin of the patient around the seeded tubular scaffold to form a neophallus with the neourethra disposed therein.

5. The method of claim 4, wherein the skin flap includes an external phallus skin flap and a de-epithelialized skin flap, and wherein the rolling comprises:
   applying a penile construction template to the donor skin of the patient, the penile construction template including
   a first section defined on an adhesive film to identify the external phallus skin flap of the donor skin to be extracted while the adhesive film is adhered to the donor skin;
   a second section defined on the adhesive film to identify the de-epithelialized skin flap of the donor skin to be extracted while the adhesive film is adhered to the donor skin; and
   removing the skin flap, including cutting out an external phallus section and the de-epithelialized skin flap from the donor skin, using the first section and the second section.

6. A method of implanting a neourethra attached to a natal urethra of a patient, comprising:
   seeding a tubular scaffold with urethral cells of the patient;
   disposing the seeded tubular scaffold within a body of the patient for in vivo growth of a neourethra; and
   connecting the neourethra to the natal urethra,
   wherein the connecting includes rolling a skin flap obtained from donor skin of the patient around the seeded tubular scaffold to form a neophallus with the neourethra disposed therein,
   wherein the skin flap includes an external phallus skin flap and a de-epithelialized skin flap, and the rolling includes:
   applying a penile construction template to the donor skin of the patient, the penile construction template including (1) a first section defined on an adhesive film to identify the external phallus skin flap of the donor skin to be extracted while the adhesive film is adhered to the donor skin, and (2) a second section defined on the adhesive film to identify the de-epithelialized skin flap of the donor skin to be extracted while the adhesive film is adhered to the donor skin; and removing the skin flap, wherein removing the skin flap includes cutting out an external phallus section and the de-epithelialized skin flap from the donor skin, using the first section and the second section.

7. The method of claim 6, wherein the connecting includes connecting the neourethra to the natal urethra using a hose barb.

8. The method of claim 6, wherein the tubular scaffold is biodegradable.

* * * * *